(12) United States Patent
Vergnault

(10) Patent No.: US 8,697,755 B2
(45) Date of Patent: Apr. 15, 2014

(54) BETA 2 ADRENERGIC RECEPTOR AGONISTS SUCH AS TERBUTALINE FOR USE IN THE TREATMENT OF NOCTURNAL HYPOGLYCEMIA

(75) Inventor: Guy Vergnault, Kembs (FR)

(73) Assignee: Jagotec AG, Muttenz (CH)

( * ) Notice: Subject to any disclaimer, the term of this patent is extended or adjusted under 35 U.S.C. 154(b) by 0 days.

(21) Appl. No.: 13/384,388

(22) PCT Filed: Jul. 16, 2010

(86) PCT No.: PCT/EP2010/060326
§ 371 (c)(1),
(2), (4) Date: Apr. 19, 2012

(87) PCT Pub. No.: WO2011/009818
PCT Pub. Date: Jan. 27, 2011

(65) Prior Publication Data
US 2012/0196938 A1    Aug. 2, 2012

(30) Foreign Application Priority Data
Jul. 21, 2009 (GB) .................................. 0912646.7

(51) Int. Cl.
*A01N 31/08* (2006.01)
*A61K 31/05* (2006.01)
*A61K 9/00* (2006.01)

(52) U.S. Cl.
USPC .......................................... 514/731; 424/400

(58) Field of Classification Search
USPC .......................................... 514/731; 424/400
See application file for complete search history.

(56) References Cited

U.S. PATENT DOCUMENTS 6,656,507 B2 * 12/2003 Petereit et al. ................. 424/490
2006/0035874 A1 * 2/2006 Lulla et al. .................... 514/171

OTHER PUBLICATIONS

Cooperberg et al. "Terbutaline and the Prevention of Nocturnal Hypoglycemia in Type 1 Diabetes." *Diabetes Care.* 31.12(2008):2271-2272.
Dahl et al. "Terbutaline Sustained-Release Tablets in Nocturnal Asthma—A Placebo Controlled Comparison Between a High and a Low Evening Dose." *Brit. J. Dis. Chest.* 82(1988):237-241.
Eriksson et al. "A Comparison of Sustained-Release Terbutaline and Ordinary Terbutaline in Bronchial Asthma." *Brit. J. Dis. Chest.* 76(1982):202-204.
Raju et al. "Nocturnal Hypoglycemia in Type 1 Diabetes: An Assessment of Preventive Bedtime Treatments." *J. Clin. Endocr. Metab.* 91.6(2006):2087-2092.
*Remington's Pharmaceutical Sciences.* Gennaro, ed. Easton, PA: Mack Publishing. 18th ed. (1990):1553-1593.
*Remington's Pharmaceutical Sciences.* Gennaro, ed. Easton, PA: Mack Publishing. 18th ed. (1990):1684-1685.
Saleh et al. "Alanine and Terbutaline in the Prevention of Nocturnal Hypoglycemia in IDDM." *Diabetes Care.* 20.8(1997):1231-1236.
Umprayn et al. "Development of Terbutaline Sulfate Sustained-Release Coated Pellets." *Drug Dev. Indust. Pharm.* 25.4(1999):477-491.

* cited by examiner

*Primary Examiner* — Benjamin Packard
(74) *Attorney, Agent, or Firm* — Mintz Levin Cohn Ferris Glovsky and Popeo, P.C.; Muriel Liberto, Esq.

(57) ABSTRACT

The invention is concerned with methods, regimens and dosage forms employing a beta 2 adrenergic receptor agonist such as terbutaline sulphate, for treating nocturnal hypoglycaemia in human subjects whilst reducing incidence of hyperglycaemia in said subjects upon wakening.

8 Claims, 4 Drawing Sheets

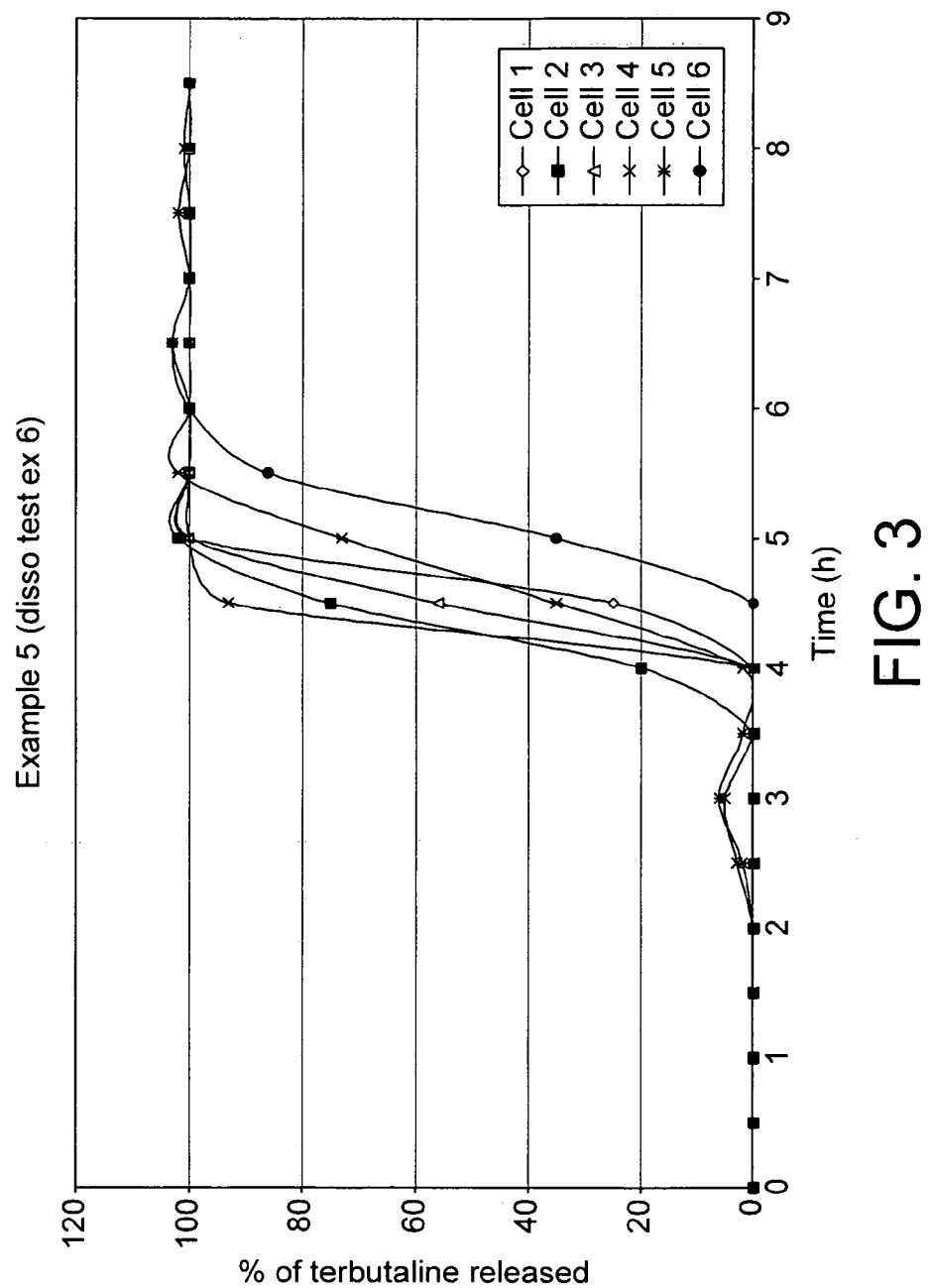

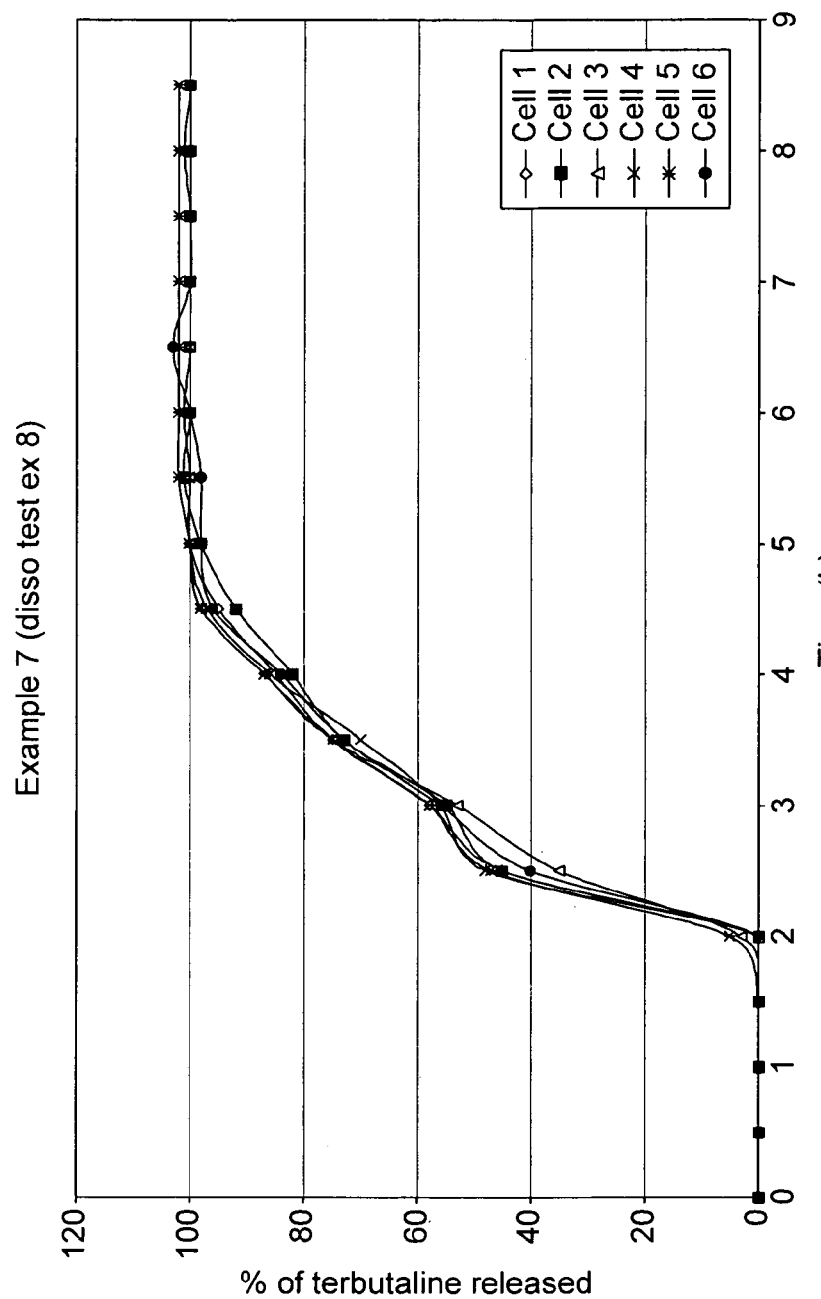

Figure 1:
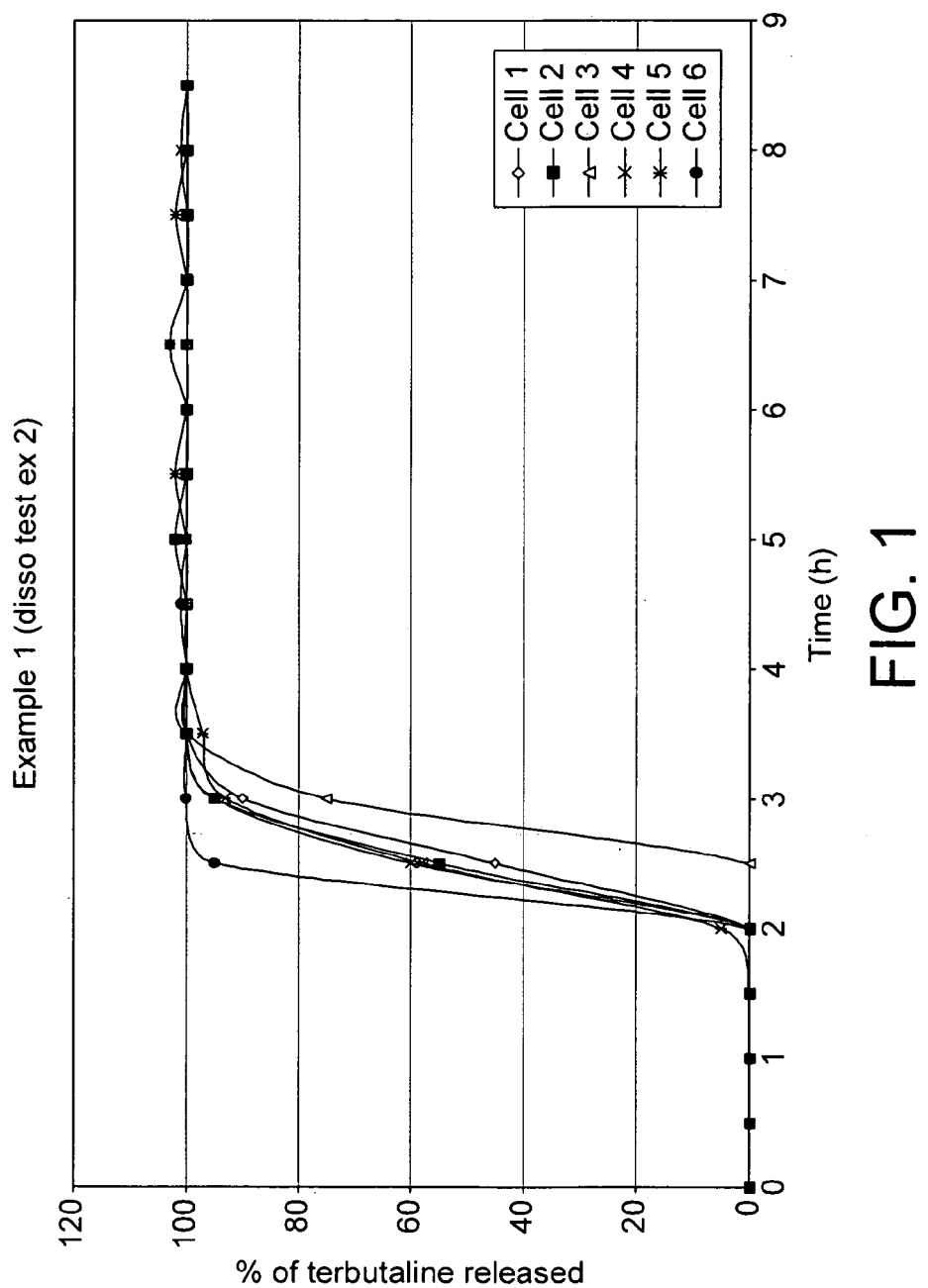

BETA 2 ADRENERGIC RECEPTOR AGONISTS SUCH AS TERBUTALINE FOR USE IN THE TREATMENT OF NOCTURNAL HYPOGLYCEMIA

RELATED APPLICATIONS

This application is a national stage application, filed under 35 U.S.C. §371, of International Application No. PCT/EP2010/060326 filed Jul. 16, 2010, which claims priority to GB 0912646.7, filed Jul 21, 2009, the contents of which are hereby incorporated by reference in their entirety.

The present invention is concerned with compositions, regimens and methods for treating nocturnal hypoglycaemia.

Hypoglycaemia can arise from many causes and can occur at any age. The most common forms of moderate and severe hypoglycaemia occur as a complication of treatment of diabetes mellitus with insulin or with certain oral medications.

Hypoglycaemia is a limiting factor in glycaemia management of diabetes. It arises in diabetic patients because of their receiving insulin or other medications. The condition is often called iatrogenic hypoglycaemia because it is occasioned by a subject's use of insulin or other medication in control of diabetes. Hypoglycaemia causes recurrent morbidity in most people with type I and many with type II diabetes.

Whereas hypoglycaemia is common in people with diabetes, it can occur for reasons not related to diabetes or its treatment. Other types of hypoglycaemia include post-prandial hypoglycaemia, which can occur approximately 4 hours after a meal; alimentary hypoglycaemia occurring as a consequence of dumping syndrome and occurring in patients that have had stomach surgery; hormonal hypoglycaemia, which is caused due to lack of hormones, i.e. hypothyroidism; hypoglycaemia caused by *heliobacter pylori* induced gastritis; hypoglycaemia caused by congenital enzyme deficiencies, such as galactosemia and hereditary fructose intolerance; Idiopathic reactive hypoglycaemia; and Late hypoglycaemia (occult diabetes characterized by a delay in early insulin release from pancreatic B cells).

Hypoglycaemia is the medical term for a condition produced by a lower than normal level of blood glucose. No single glucose value alone serves to define the condition for all people and purposes, and the level considered low enough to be defined as hypoglycaemia will depend on various factors such as the measurement method, the subject's age, and the presence or absence of effects. For healthy humans, in any given 24 hour period glucose levels are generally maintained within a range of 70-150 mg/dL. 60 or 70 mg/dL is commonly considered as the lower limit of normal glucose, although different values (typically below 40, 50, 60, or 70 mg/dL) have been defined as low for different populations, clinical purposes, or circumstances.

Diabetes adversely affects the way the body uses sugars and starches which, during digestion, are converted into glucose. Insulin, a hormone produced by the pancreas, makes the glucose available to the body's cells for energy. In muscle, adipose and connective tissues, insulin facilitates the entry of glucose into the cells by an action on the cell membranes. The net effect of insulin is to promote the storage and use of carbohydrates, protein and fat. Insulin deficiency is a common and serious pathologic condition in man. In Type I diabetes the pancreas produces little or no insulin, and insulin must be injected daily for the survival of the diabetic. In Type II diabetes the pancreas produces insulin, but the amount of insulin is insufficient, or less than fully effective due to cellular resistance, or both.

Hypoglycaemic symptoms are manifold and will depend on the severity of the condition and other factors. Symptoms include shakiness, anxiety, nervousness, tremor, palpitations, tachycardia, sweating, feeling of warmth, pallor, coldness, clamminess, dilated pupils (mydriasis), feeling of numbness (parasthaesia) in the fingers, hunger, nausea, vomiting, abdominal discomfort, headache, abnormal mentation, impaired judgment, non-specific dysphoria, anxiety, moodiness, depression, crying, negativism, irritability, belligerence, combativeness, rage, personality change, emotional lability, fatigue, weakness, apathy, lethargy, daydreaming, confusion, amnesia, dizziness, delirium, staring, "glassy" look, blurred vision, double vision, difficulty speaking, slurred speech, ataxia, lack of coordination, focal or general motor deficit, paralysis, hemiparesis, stupor, coma, abnormal breathing and generalized focal seizures.

Not all of the above manifestations occur in every case of hypoglycaemia. There is no consistent order to the appearance of the symptoms, if symptoms even occur. Specific manifestations may also vary by age, by severity of the hypoglycaemia and the speed of the decline.

Hypoglycaemia is usually treated quite simply by the administration of dextrose or foods quickly digestible to glucose. However, a problem particularly frequently encountered by patients suffering from diabetes, is the nocturnal drop in blood glucose levels, so-called nocturnal hypoglycaemia. In mild cases this results in nothing more than morning dizziness or occasionally nausea. Sometimes however, blood glucose levels drop so low during the night or early in the morning that the state of hypoglycaemia becomes severe, leading to unconsciousness or convulsions. Importantly, severe hypoglycaemia is more likely to occur at night when the patient is asleep, rather than during the day, when the patient can feel the onset of hypoglycaemia and prevent it by eating carbohydrates, e.g. a lump of sugar or specific glucose tablets, energy gels or bars marketed for diabetic patients. Moreover, both mild and severe hypoglycaemia predisposes the patient to a condition known as hypoglycaemic unawareness, which in turn means that hypoglycaemia can occur more frequently and at any time of the day, due to attenuation of the typical warning symptoms of a declining blood glucose level, e.g. hunger, perspiration or one or more of the other symptoms already mentioned.

Nocturnal hypoglycaemia is particularly serious because it coincides with longest interprandial period and the longest time between self-monitoring of blood glucose.

Current treatments are limited and only partially effective. They include administering snacks at bedtime, including corn starch, to produce more sustained exogenous glucose delivery overnight. Administration of alpha-glycosidase inhibitor to delay the digestion of carbohydrates in the evening meal or glucagon administered either subcutaneously, intramuscularly, or intranasally, which activates glycogenolysis and to some extent gluconeogenesis with an increase of glucose production.

Current measures to produce sustained endogenous glucose production only achieve normo-glycaemia for less than 2 hours. Glucagon administered only lasts for 60 to 120 minutes and should be avoided in Diabetes type II patients because it can stimulate endogenous insulin secretion. These measures may help to prevent occurrence of hypoglycaemia in the early hours of sleep, but they are relatively ineffective in treating this condition over the full sleep period.

Recent studies have looked into the possibility of using oral terbutaline as a means of controlling nocturnal hypoglycaemia in diabetes mellitus patients treated with insulin.

Terbutaline, in its sulphate salt form, is available in 2.5 mg (2.05 mg as free base) and 5 mg (4.1 mg as free base). It is indicated for the relief of bronchospasm associated with chronic obstructive pulmonary disease, for the prevention of and reversal of bronchospasm in patients 12 years of age and older with asthma and reversible bronchospasm associated with bronchitis and emphysema, and for the management of pre-term labour. It is a member of a class of substances called beta 2 adrenergic receptor agonists. Other is representative members of the class include salbutamol (albuterol in the US), bitolterol mesylate, formoterol, isoprenaline, levalbuterol, metaproterenol, salmeterol, dobutamine, dopamine, epinephrine, norepinephrine and ritodrine.

In a study reported in The Journal of Endocrinology and Metabolism 91(6): 2087-2092 2006, 5 mg terbutaline sulphate tablets ("Brethine" Novartis, which is an immediate release dosage form) were investigated as a putative treatment for nocturnal hypoglycaemia in patients with type I diabetes. The tablets were administered without any other conventional treatments, e.g. snacks or the like. It was concluded that whereas the tablets prevented nocturnal hypoglycaemia over the full sleep period, unfortunately subjects developed hyperglycaemia upon wakening. It also raised heart rate and blood lactate concentrations.

A subsequent study reported in Diabetes Care Vol 31, No. 12, 2271-2272 December 2008 investigated a similar immediate release tablet but at lower dose (2.5 mg "Brethine" Novartis). The effect of the lower dose suggested a dose proportional effect as its impact on hypoglycaemia was intermediate between the 5 mg dose and no dose at all. However, the investigators were unable to confirm from the study if the lower dose prevented hyperglycaemia in subjects upon wakening.

The use of terbutaline sulphate as a potential therapy for nocturnal hypoglycaemia is still unclear. A higher 5 mg dose of an immediate release form administered at bedtime caused hyperglycaemia in subjects upon wakening. But lowering the dose of the same immediate release dosage form in an attempt to address these hyperglycaemia events reduced the effectiveness in treating hypoglycaemia, without conclusively demonstrating that hyperglycaemia in the morning upon wakening can be avoided.

Unfortunately, there is currently no pharmacological treatment available to prevent the occurrence of nocturnal hypoglycaemia over a sleep cycle. As such, there remains a need to provide a treatment that addresses this condition and which at the same time does not result in subjects developing hyperglycaemia upon wakening.

Applicant has found that a modified release formulation of terbutaline sulphate or other beta-2 adrenergic receptor agonist may be useful in treating nocturnal hypoglycaemia and also overcome the reported side effects to produce a more pronounced normoglycaemic effect during the night and avoiding morning hyperglycaemia. The benefits of such a treatment are clearly useful to treat nocturnal hypoglycaemia whatever its cause, but is particularly useful for type I and type II diabetes patients where hypoglycaemia has been a recurring problem and presents severe safety risks. It also is useful for a larger population of diabetics treated with insulin to allow for more aggressive blood glucose control without increasing the risk of hypoglycaemia. More aggressive glucose control therapy usually includes setting specific goals for maintaining blood sugar levels within a certain range before and after meals and attempting to achieve a quarterly haemoglobin A1c (test measuring average glucose over a three-month period) of less than about 7%. Glucose control therapy requires frequent injections of insulin, close monitoring of dietary habits, regular use of exercise and frequent blood sugar tests.

The present invention provides dosage forms, regimens and methods, which provide for the treatment of nocturnal hypoglycaemia in patients without eliciting, or at least minimizing, adverse effects such as hyperglycaemia upon wakening in the morning and/or worsening glucose control.

In a first aspect of the present invention there is provided a method of treating nocturnal hypoglycaemia with a modified release oral dosage form containing terbutaline sulphate, and simultaneously preventing or reducing the incidence of hyperglycaemia in a subject upon wakening.

In another aspect of the invention there is provided a method of treating nocturnal hypoglycaemia with an oral dosage form containing terbutaline sulphate, wherein said oral dosage form, when tested in a group of human subjects provides a time ($T_{max}$) to mean peak plasma concentration ($C_{max}$) between 1 hour and 6 hours of administration of said dosage form.

In another aspect of the invention there is provided a method of treatment of nocturnal hypoglycaemia with an oral dosage form containing terbutaline sulphate wherein the dosage form, when tested in a group of human subjects, achieves for a dose of 5 mg a mean peak plasma concentration (Cmax) of terbutaline thereof, of about 3 to 9 ng/ml, and a mean $AUC_{0-48}$ of about 14 to 68 hr.ng/ml.

Terbutaline sulphate is employed in oral dosage forms, but the active agent of terbutaline sulphate is actually the free base terbutaline. By "active agent" as used in relation to the terbutaline sulphate or any other beta 2 adrenergic receptor agonist is meant the beta 2 adrenergic receptor agonist itself in the form in which it is loaded into an oral dosage form if this is the pharmaceutically active moiety, or insofar as the beta 2 adrenergic receptor agonist administered in the dosage form is transformed, e.g. metabolised in-vivo, it refers to this active species or metabolite.

Oral terbutaline sulphate exhibits substantial dose proportionality with respect to AUC and $C_{max}$. For example, a 2.5 mg dose of terbutaline sulphate will provide a mean $AUC_{0-48}$ of about 7 to 34 hr.ng/ml. Furthermore, as there is substantial dose proportionality, the skilled person is able to obtain Cmax and AUC for other doses by extrapolation or interpolation from the values provided above. By way of further example a 1.0 mg dose of terbutaline sulphate will provide a mean $AUC_{0-48}$ of about 3 to 14 hr.ng/ml. A 0.1. mg dose of terbutaline sulphate will provide a mean $AUC_{0-48}$ of about 0.3 to 1.4 hr.ng/ml.

The pharmacokinetic parameters $T_{max}$ $C_{max}$ and AUC are terms well known in the art. $T_{max}$, $C_{max}$ and AUC can be obtained by plotting blood plasma concentrations of a drug (Y-axis) against time (X-axis). $C_{max}$ is the observed maximum of this plot and $T_{max}$ is the time to the observed $C_{max}$. $AUC_t$ corresponds to the area under the curve up to certain sampling points (or extrapolated in some cases) and reflects the bioavailability of the drug for a given route of administration. These values are typically measured as mean values The term "mean" as used herein in relation to these pharmacokinetic parameters represents the arithmetic mean value measure across a patient population (usually at least 10 patients).

In another aspect of the invention there is provided a method of treatment of nocturnal hypoglycaemia with an oral dosage form containing terbutaline sulphate wherein the oral dosage form, when tested in an in-vitro simulated intestinal fluid, releases the beta 2 adrenergic receptor agonist over a period of time defined by an in-vitro dissolution profile wherein not more than 10% of the dose of terbutaline sulphate is released after 1 or 2, hours; at least 80% released after 6 hrs, and at least 100% released after 10 hours The sleep patterns of children and adults can differ substantially. Children generally go to bed earlier than adults and the duration of their sleep tends to be longer than adults. Accordingly, the release profiles described above may be tailored for different patient populations.

In a particular embodiment, particularly suitable for children, there is provided a method of treatment of nocturnal hypoglycaemia with an oral dosage form containing terbutaline sulphate wherein the oral dosage form, when tested in an in-vitro simulated intestinal fluid, releases terbutaline sulphate over a period of time defined by an in-vitro dissolution profile wherein not more than 10% of the dose of terbutaline sulphate is released after 1 or 2 hours; at least 50% released after 4 hrs, and at least 80% released after 8 hours.

In another embodiment there is provided a method of treatment of nocturnal hypoglycaemia with an oral dosage form containing terbutaline sulphate wherein the oral dosage form, when tested in an in-vitro simulated intestinal fluid, releases terbutaline sulphate over a period of time defined by an in-vitro dissolution profile wherein not more than 10% of the dose of terbutaline sulphate is released after 1 or 2 hours, at least 80% released after 4 hrs, and at least 100% released after 6 hours.

The simulated intestinal fluid (SIF) is an aqueous phosphate buffer solution at a pH of 6.8. A suitable simulated fluid for this purpose consists of 68.05 g of potassium dihydrogen phosphate and 8.96 g of sodium hydroxide dissolved in 10 liters of deionized water. As an alternative to SIF one may employ purified water as the dissolution medium. The in-vitro test may be carried out in accordance with the USP apparatus II with paddle rotation at 100 rpm.

The USP monograph for terbutaline sulphate tablets recommends USP apparatus I. However, USP Apparatus II is the preferred method for the purpose of the present invention as the dosage form is intended to be released in the lower GI tract and will be subjected to relatively high mechanical stress during transit prior to release. USP II apparatus at 100 rpm creates particularly high turbulent forces that better reflect the forces on the oral dosage form in-vivo. Stationary baskets could be used to maintain the dosage form in the high turbulence zone located under the paddle.

Procedures for carrying out in-vitro dissolution tests are well known in the art. Typically a dissolution apparatus may be set by programming the temperature, rotation and run time at 37 degrees centigrade, 100 rpm and 12 hours. 900 ml of dissolution medium is placed in each of six vessels of the dissolution apparatus. The apparatus is assembled and the dissolution medium is equilibrated to 37 degrees and the thermometer is removed. One unit dosage form is placed in each of the six vessels. Rotation of the paddle is started at the speed of 100 rpm for 12 hours. Aliquots (each of 6 ml) are withdrawn, and successively replaced with equal volumes of fresh dissolution medium, at the desired interval periods from each of the six vessels.

The amount of dissolved terbutaline sulphate can be determined conventionally by HPLC. Detection can be by UV absorption at a wavelength of 235 nm. Quantification can be effected by comparison of HPLC peak height (or area) with the peak height (or area) taken from a standard plot of concentration vs. peak height (or area) for standards of known concentration.

The test preparations are separately injected into the chromatograph after filtering through 0.45 [mu]m membrane filter. Chromatograms are recorded and the peak responses of the test peak are compared in terms of area with a standard. The quantity of beta-2 adrenergic receptor agonist released in percent (%) can then be calculated.

In another aspect of the invention there is provided a method of treating nocturnal hypoglycaemia using a modified release dosage form containing terbutaline sulphate, wherein the oral dosage form is adapted for oral administration according to a schedule wherein 0.1 to 10 mg of terbutaline sulphate is administered to a subject once a day before bedtime.

By "bedtime" as this term relates to the dosing schedule described above, is meant a period immediately before a subject retires to bed for sleep. This period may differ from subject to subject, and substantially when comparing children's sleeping habits with adults. More particularly, bedtime is between about 7 pm to midnight, still more particularly about 7 to 9 pm for children and between 10 pm and midnight for adults.

In another aspect of the invention there is provided a method of treating nocturnal hypoglycaemia using a modified release dosage form containing terbutaline sulphate, adapted for oral administration according to a schedule whereby 0.1 to 10 mg dose of terbutaline sulphate once a day before bedtime and taken either simultaneously with food or after food.

It is preferred to administer the dosage form without food, more preferably at least 15 to 30 minutes before any food intake, to prevent as much as possible the release of drug in the presence of food that could negatively impact its bioavailability. Dosing in this way it is possible to avoid food-drug interactions that may result in the reduced, delayed or increased systemic availability of the drug. This food-drug interaction is often referred to as a "food effect". Drug products that display no food effect are those in which the Cmax, Tmax or AUC do not differ, or only differ within margins generally accepted by health authorities such as the FDA, as is generally known in the art.

In another aspect of the invention there is provided a method of treating nocturnal hypoglycaemia with an oral dosage form containing terbutaline sulphate wherein said dosage form, upon administration to a subject in need of treatment, releases terbutaline sulphate after a lag time of at least 1 hour, more particularly 2 hours during which lag time none, or substantially none, of the terbutaline sulphate is released.

The methods referred to herein are useful in the treatment of nocturnal hypoglycaemia, however the condition is caused and in any patient population. In particular, the methods described herein are useful in the treatment of nocturnal hypoglycaemia in patients being treated for type I or type II diabetes. Still further, reactive hypoglycaemia (hypoglycaemia a few hours after a meal) fasting hypoglyacaemia (hypoglycaemia on an empty stomach), hypoglycaemia caused by oral diabetes drugs, beta-blockers or other drug interactions, hypoglycaemia caused by insulin-secreting pancreatic tumour, alcohol-induced hypoglycaemia, alimentary hypoglycaemia (rapid jejunal emptying with exaggerated insulin response), hypoglycaemia after gastrectomy, tumour hypoglycaemia, hormonal hypoglycaemia (e.g. acquired adrenal insufficiency or acquired hypopituitarism), immunopathologic hypoglycaemia, or hypoglycaemia caused by congenital enzyme deficiencies such as galactosemia and hereditary fructose intolerance The methods described herein are useful in the treatment of nocturnal hypoglycaemia, a contributory cause of which is the use of another medication, whether taken to treat diabetes or otherwise. Examples of such medication include but are not limited to insulin or other antidiabetic medications including oral hyperglycaemic agents, ethanol, Beta blockers, e.g. propranolol, salicylates, Acetaminophen, Acetazolamide, Aluminium hydroxide, Chloroquine, Chlorpromazine, Cimetidine, ranitidine, Diphenhydramine, Propoxyphene, Disopyramide, Doxepin, Isoxsuprine, Insulin-like growth factor 1, Lidocaine, Lithium, Pentamidine, Propranolol, nadolol, labetalol, metoprolol, Orphenadrine, Oxytetracycline, Quinine, quinidine, Perhexiline, Ritodrine, Haloperidol, Chelating agents, Colchicine, Para amino benzoic acid, para-amino salicylic acid, Cholestyramine added during glucocorticoid therapy (reduces absorption), Drugs which lower glucose in diabetics mentioned above, Enalapril and captopril, Coumarin, Phenylbutazone, Antihistamines, Sulfa antibiotics, Monoamine oxidase inhibitors, Azapropazone, buformin, carbutamide, cibenzoline, cycloheptolamide, glibornuride, gliclazide, mebanazine, metahexamide, perhexiline, sulphadimidine and sulphaphenazole.

For the purpose of the present invention, such medications described above are considered to be a "first medication".

In another aspect of the present invention there is provided a method of treating nocturnal hypoglycaemia in a patient in need thereof comprising the step of (a) determining if said patient is undergoing treatment with one or more of a first medication and (b) administering an oral dosage form comprising terbutaline sulphate to said patient based on said patient's treatment with said one or more first medication.

The first medication could be a medication used to treat diabetes, in which case, terbutaline sulphate may be used as an adjunctive therapy to this first medication, or the first medication could be administered to treat a condition other than diabetes.

In yet another aspect of the invention said methods described hereinabove employ a dosage form in a kit comprising packaging or labelling advising subjects regarding one or more first medication, or advising on dosing relative to the use of said one or more first medication.

The invention also provides as further aspects of the invention dosage forms describe herein for use in the methods described hereinabove.

The invention in still further aspects provides uses of dosage forms described herein in the methods described hereinabove.

Still further, the invention provides the use of terbutaline sulphate in the manufacture of dosage forms described herein for use in the methods of treatment of nocturnal hypoglycaemia described herein above.

The aspects of the invention described herein above may be read alone as sole aspects of the invention or they may be read together in any combination to form other particular aspects of the invention.

The dosage form employed in the present invention is adapted to release terbutaline sulphate according to a modified release profile. Modified release dosage forms are defined by the USP as those whose drug release characteristics of time course and/or location are chosen to accomplish therapeutic or convenience objectives not offered by conventional immediate release dosage forms.

In particular, dosage forms of the present invention are adapted to release terbutaline sulphate after a pre-determined lag time, during which none, or substantially none, of the terbutaline sulphate is released.

In a particular embodiment the dosage form releases the drug in a time-dependent manner, that is, drug release is independent of any changes in the physiological environment surrounding the dosage form, such as a change in pH or temperature or enzymatic or food conditions.

The lag time may be from 1 to 6 hours, still more particularly from 2 to 3 hours.

During the lag time none, or substantially none, of the dose of terbutaline sulphate is released. By the phrase "none or substantially none" as it relates to the release of a drug from a dosage form described herein, is meant that if any of the drug is released it is in such small amounts that therapeutically effective blood plasma levels of terbutaline sulphate or the active agent thereof are not reached. In particular, in so far as any dose is released, it is no more than about 10%, still more particularly no more than about 5%, more particularly no more than about 1%.

Following the expiry of the lag time, the drug begins to be released from the dosage form. The drug may for example be released rapidly or may be released slowly over a period of time (controlled release), or it may be dual released, that is an rapid release, followed by a slow release, or slow followed by rapid release.

The invention has been described with reference to terbutaline sulphate as the drug contained in the oral dosage form. However, terbutaline sulphate is a member of the class of beta-2-adrenergic receptor agonist and other members of this class of drugs may be employed in the present invention including salbutamol (albuterol in the US), bitolterol mesylate, formoterol, isoprenaline, levalbuterol, metaproterenol, salmeterol, dobutamine, dopamine, epinephrine, norepinephrine and ritodrine.

The dosage amounts in which any of these other beta 2 adrenergic receptor agonists may be employed in the present invention will depend largely on the particular compound employed, the condition of the subject, and the nature and severity of the condition to be treated. Typically, they will be employed in oral dosage forms of about 0.1 to 500 mg.

Examples of dosage forms adapted to release a pharmaceutical dosage after a lag time are known in the art. They have been proposed for use in treating morning conditions, diseases, or illnesses, such as arthritis, hypertension and asthma, the symptoms of which are generally acute in the morning as the patient awakens from sleep. These dosage forms are potentially very convenient for patients as they can be taken before bedtime and arrest symptoms that occur upon wakening. Without this type of pharmacological intervention patients would be required to either disturb their sleep to administer a conventional dosage form prior to their normal wakening time, or remain un-medicated and suffer the morning symptoms.

Nocturnal hypoglycaemia is not such a morning condition, disease or illness. It is a condition that occurs as a patient sleeps. It is a condition that is associated with substantial morbidity and mortality and it is important to recognise, diagnose and treat properly. In certain circumstances, if the symptoms do not cause the patient to wake, the patient remains unaware of the developing symptoms and uncontrolled. In such cases, the treatment's effectiveness, or lack thereof, can only be determined once the patient awakens from sleep when it is too late to arrest the symptoms and in severe cases emergency treatment may be called for to treat acute symptoms.

The dosage forms useful in the present invention are adapted for oral administration and may take any form conventional in the art, that is, they may be in the form of tablets, capsules, multi-particulates in sachet or encapsulated form, syrups and the like.

Dosage forms of the present invention, after expiry of the lag time, may vary in release rate characteristics from immediate release to controlled release, or a mixed profile of immediate release and controlled release. Release may be continuous or pulsatile.

Excipients are employed in the oral dosage form to optimise the bulk properties of the dosage form and to affect the desired release profile. These excipients typically include diluents or fillers, which add bulk to a formulation to enable formulations of a desired size to be prepared; binders or adhesives, which promote the adhesion of the particles of a formulation to maintain the integrity of the dosage form; disintegrants or disintegrating agents, which promote the break-up of the dosage form after ingestion to make the ingredients more readily available; anti-adherents, glidants or lubricants, which enhance the flow of the tableting materials, for example into tablet dies, prevent sticking of the formulation to tablet-making machinery; and miscellaneous adjuvants such as colourants and flavourants.

Suitable diluents include pharmaceutically acceptable inert fillers such as microcrystalline cellulose, lactose, dibasic calcium phosphate, saccharides, and/or mixtures of any of the foregoing. Examples of diluents include microcrystalline cellulose such as Avicel grades, PH101 PH102 ,PH112, PH113, PH200, PH300, PH301, PH xxx HFE PHxxx CE; lactose such as lactose monohydrate, lactose anhydrous, and Pharmatose DCL 21; dibasic calcium phosphate such as Emcompress; mannitol; starch; sorbitol; fructose; sucrose; and glucose. Diluents are carefully selected to match the specific requirements of the formulation. The diluent is preferably used in an amount of 10% to 90% by weight, more particularly 50% by weight, of the dosage form.

Suitable lubricants and glidants, including agents that act on the flowability of the powder to be compressed are, for example, colloidal silicon dioxide such as Aerosil 200, Cab O Sil; talc; stearic acid, magnesium stearate, calcium stearate, sodium stearyl fumarate, polyethylene glycol and sodium lauryl sulphate. The lubricant is preferably used in an amount of 0.5 to 2% by weight, in particular 1% by weight, of the dosage form.

Suitable binders include polyethylene glycols such as PEG 6000; cetostearyl alcohol; cetyl alcohol; polyoxyethylene alkyl ethers; polyoxyethylene castor oil derivatives; polyoxyethylene sorbitan fatty acid esters; polyoxyethylene stearates; poloxamers; waxes, alginic acids and salts thereof; HPC; HPMC; methylcellulose; maltodextrin and dextrin; povidone; gums; starch and modified starches. The binder preferably may be used in an amount of 2 to 10% by weight, more particularly 5% by weight, of the dosage form.

Suitable disintegrants include sodium starch glycolate, such as Explotab, crospovidone such as Kollidon CL, polyplasdone XL, sodium carboxymethylcellulose, sodium croscarmellose such as AcDiSol, and starch. The disintegrant preferably may be used in an amount of 2 to 10% by weight, more particularly 5% by weight, of the dosage form.

If an immediate burst of the dose of beta 2 adrenergic receptor agonist is required upon expiry of the lag time, the dosage form may comprise a surface-active agent such as sodium lauryl sulfate, sodium monoglycerate, sorbitan monooleate, polyoxyethylene sorbitan mono-oleate, glyceryl monostearate, glyceryl mono-oleate, glyceryl monobutyrate, any one of the Pluronic line of surface-active polymers, or any other suitable material with surface active properties or any combination of the above.

Surface active materials may be present in the dosage form in amounts of 0.1 to 10% by weight.

The total excipients employed may be present in the dosage form in amounts of 10 to 99.99% by weight.

Additional examples of pharmaceutically acceptable carriers and excipients that can be used to formulate oral dosage forms are described in the Handbook of Pharmaceutical Excipients, American Pharmaceutical Association.

The term controlled release as it relates to a dosage form of the present invention refers to a the dosage form, or a part thereof comprising a phase that is adapted to release a dose of beta 2 adrenergic receptor agonist within a certain time to accomplish a therapeutic objective not possible using a conventional immediate release phase.

The controlled release phase or matrix may contain any of the aforementioned excipients described above in the amounts already mentioned. However, in addition the controlled release phase should contain a release rate controlling agent or agents.

The term "release rate controlling agent" includes any agent or agents that alone or in combination, optionally together with other excipients, controls the rate of release of a dose of beta 2 adrenergic receptor agonist in terms of duration in order to give a therapeutic effect not possible with a conventional immediate release formulation, and includes hydrophilic polymers, hydrophobic polymers or mixtures thereof, or copolymers thereof, or mixtures of these polymers and copolymers.

The release controlling agent may be in a matrix in which the beta 2 adrenergic receptor agonist is dissolved or dispersed. Alternatively, the release controlling agent may be in a layer or coating surrounding a matrix containing the beta 2 adrenergic receptor agonist. Still further, it may be employed in a matrix and a coating. When the release controlling agent is in the layer or coating, the matrix may also contain a release controlling agent, or it may be adapted for immediate release, or a mixture of both.

By selecting appropriate matrix and/or coating materials one is able not only to accurately control the lag time, one is also able to ensure that all, or substantially all, of the dose of a beta 2 adrenergic receptor agonist upon expiry of the lag time is released at a desired rate to achieve a desired therapeutic effect.

Examples of release-rate controlling agents to be used in this invention include hydroxyalkylcellulose, such as hydroxypropylcellulose and hydroxypropylmethylcellulose; poly (ethylene)oxide; alkylcellulose such as ethycellulose and methylcellulose; carboxymethylcellulose; hydrophilic cellulose derivatives; polyethylene glycol; cellulose acetate; cellulose acetate butyrate; cellulose acetate phthalate; cellulose acetate trimellitate; polyvinylacetate phthalate; hydroxypropylmethylcellulose phthalate; hydroxypropylmethylcellulose acetate succinate; poly(alkyl methacrylate); and poly (vinyl acetate). Other suitable hydrophobic polymers include polymers or copolymers derived from acrylic or methacrylic acid esters, copolymers of acrylic and methacrylic acid esters, zein, waxes, shellac and hydrogenated vegetable oils.

The release-rate-controlling agent may include a hydroxypropyl methylcellulose (HPMC), a hydroxypropyl cellulose (HPC), a poly(ethylene oxide), an ethylcellulose or a combination thereof, in particular present in an amount of 5 to 90% based on the weight of the dosage form.

Preferred types of HPMC for use in accordance with the invention are those sold under the trademark Methocel (Dow Chemical Co.). Suitable Methocels include the K grades such as Methocel K 15M, Methocel K 100M, Methocel K 100LV and Methocel K 4M. Other suitable Methocels include the E, F and J grades.

As HPCs there can be employed those sold under the trademark Klucel (Hercules, Inc.) or equivalents. Suitable Klucels include Klucel LF, Klucel JF, Klucel GF, Klucel MF and Klucel HF.

As poly(ethylene oxide)s there may be mentioned those sold under the trademark Sentry Polyox (Union Carbide Corp.) or equivalents. Suitable Polyoxs include the Polyox WSR grades such as Polyox WSR Coagulant, Polyox WSR-301, Polyox WSR-303, Polyox WSR N-12K, Polyox WSR N-60K, Polyox WSR-1105, Polyox WSR-205 and Polyox WSR N-3000.

As ethylcelluloses for use in accordance with the invention there can be mentioned those sold under the trademark Ethocel (Dow Chemical Co.) or equivalents.

The hydroxypropylmethylcelluloses preferably have a viscosity (2 wt % solution at 20.degree. C.) of about 5 to 100,000 mPa*s, preferably 4,000 to 100,000 mPa*s. Especially suitable are Methocel K types or their equivalents. The hydroxypropylcelluloses used according to the invention preferably have a number average molecular weight of about 80,000 to 1,150,000, more preferably 80,000 to 600,000.

Poly(ethylene oxide) preferably have number average molecular weights of about 100,000 to 7,000,000, more preferably 900,000 to 7,000,000. Especially suitable is Polyox WSR Coagulant, which has a molecular weight of 5,000,000. The ethylcelluloses used according to the invention preferably have a viscosity of about 3 to 10 mPa*s, more preferably 7 to 100 mPa*s.

Additional example of materials or excipients that may form part of a controlled release matrix are contained in Remingtons Pharmaceutical Sciences, 18th ed. Mack Publishing Co., Easton, Pa., 1990, p. 1684-1685), which is incorporated herein in its entirety for this purpose.

The dosage form may be configured in any suitable manner having regard to the particular release profile that is sought. For example, the dosage form may be monolithic, containing the beta 2 adrenergic receptor agonist in an immediate release matrix, employing any of those materials or excipients useful in an immediate release phase referred to hereinabove, or the phase may be adapted for controlled release. Alternatively, the dosage form may be multi-layered, and the layers may be arranged sandwich-like or in a concentric arrangement and the layers may be adapted to deliver the beta 2 adrenergic receptor agonist with immediate release or with controlled release. Still further, the core may comprise an immediate release matrix in which is dispersed one or more discrete phases adapted for controlled release. Still further, the dosage form may be in the form of multi-particulates some of which are adapted form immediate release and some for controlled release. The skilled person will appreciate that there is a wide variety of possible configurations for the dosage forms and the particular configuration will depend on the desired release profile.

Dosage forms of the present invention may be coated with a non-functional coating or coatings, that is a coating that does not influence the lag time or release rate of the dosage form of the uncoated formulation. Such coatings include those employed to achieve an aesthetic effect (e.g. an attractive colour or pleasant taste) or information effect, e.g. a coating may be coloured to act as a visual cue for a patient identification of a medicament. Coatings may also be over-written with information relating to the dosage, or they may elicit a handling effect, e.g. a smooth coating for ease of swallowing, or a stability effect, e.g. a moisture or light barrier during storage.

In order to facilitate the preparation of dosage forms described above there is provided, in a further aspect of the present invention, a process for the preparation of a dosage form useful in the present invention.

Dosage forms may be prepared by treating a beta 2 adrenergic receptor agonist with one or more pharmaceutically acceptable excipients, and formulating the resultant mixture into the desired dosage form using techniques well known in the art.

Techniques and compositions for making tablets (compressed and molded), capsules (hard and soft gelatin) and pills are also described in Remington's Pharmaceutical Sciences, 18th ed. Arthur Osol, 1553-93 (1990), which is incorporated herein in its entirety for this purpose.

Techniques include melt-granulation, wet granulation, dry blending, dry granulation, co-precipitation, extrusion and melt extrusion.

When the dosage form is in the form of a tablet, the tablet can be prepared by either direct compression, dry granulation (slugging and roller compaction), or by wet granulation. Wet granulation techniques may be either aqueous or non-aqueous. Non-aqueous solvents may be selected from a group comprising ethanol, isopropyl alcohol, acetone or methylene chloride.

Dosages in the form of tablets may be made by compression methods by the application of high pressures to powders or granulates utilizing steel punches and dies. In this manner a wide variety of shapes, sizes and surface markings can be formed depending on the size and design of the punches and dies employed. On an industrial scale they may be produced using rotary presses, e.g. a Manesty press, Liverpool, United Kingdom or a Korsch and Killian press, Berlin, Germany. Presses generally operate at pressures of about 1000 to about 5000 kg/cm$^2$ Dry granulation (formed by slugging or roller compaction) involves the compaction of powders at high pressure into large tablet compacts. Granulates may also be formed by pressing/pushing powders between rollers of a chilsonator to form thin and dense ribbons. These compacts are then milled and screened to form granulates of the desired particle size.

Wet granulation is a technique widely employed in the art and comprises the steps of i) weighing and blending pharmaceutical ingredient and excipients; ii) preparing a damp mass from the ingredients and excipients; iii) screening the mass into pellets or granules; iv) drying the granulate; v) sizing the granulate by screening; vi) adding lubricant as appropriate and blending; and vii) tableting by compression.

Should coating of the compositions be required, this can be achieved using conventional coating techniques such as press coating, spray coating, pan coating or air suspension coating techniques generally known in the art. All of the techniques discussed above are described in detail in Ansel's Pharmaceutical Dosage Forms and Drug Delivery Systems, Chapter 7, Seventh Edition, 1999 (Lippincott Williams & Wilkins), which is herein incorporated by reference for this purpose.

Any of the dosage forms described may be employed in the present invention. However, a particular dosage form useful in the present invention is provided in the form of a coated tablet, more particularly a press-coated tablet.

The particular dosage form may be in the form of a unit dosage form containing the entire dose of the beta 2 adrenergic receptor agonist, or it may comprise a plurality of mini-tablets or particles, which together contain the entire dosage of the beta 2 adrenergic receptor agonist. Mini tablets or particles may be contained in capsule or some other convenient form such as a sachet.

The coated tablet comprises a core containing beta-2 adrenergic receptor agonist, and a coating surrounding said core.

The core may be configured in any suitable manner having regard to the particular release profile that is sought after the lag time. For example, the core may be monolithic, containing the beta 2 adrenergic receptor agonist in an immediate release phase, employing any of those excipients referred to hereinabove, or the phase may be adapted for controlled release. Alternatively, the core may be multi-layered, and the layers may be arranged sandwich-like or a concentric arrangement and the layers may be adapted to deliver the beta 2 adrenergic receptor agonist with immediate release or with controlled release, or immediate and controlled release in a sequential manner. Still further, the core may comprise an immediate release matrix in which is dispersed one or more discrete phases adapted for controlled release. The skilled person will appreciate that there is a wide variety of possible configurations for the core and the particular configuration will depend on the desired release profile.

The coating is adapted to provide a barrier to the egress of the beta 2 adrenergic receptor agonist contained in the core until the lag time has expired.

Preferably, the coating comprises one or more water insoluble or poorly soluble hydrophobic excipients. Preferably these excipients are selected from fatty acids or their esters or salts; long chain fatty alcohols; polyoxyethylene alkyl ethers; polyoxyethylene stearates; sugar esters; lauroyl macrogol-32 glyceryl, stearoyl macrogol-32 glyceryl, and the like.

Other excipients that provide a hydrophobic quality to coatings may be selected from any waxy substance known for use as tablet excipients. Preferably they have a HLB value of less than 5, and more preferably about 2. Suitable hydrophobic agents include waxy substances such as carnauba wax, paraffin, microcrystalline wax, beeswax, cetyl ester wax and the like; or non-fatty hydrophobic substances such as calcium phosphate salts, e.g. dibasic calcium phosphate.

Coatings comprising the aforementioned materials provide for a lag time by acting as a barrier to the ingress of a physiological medium. Once the medium crosses the coating and enters the core, it may cause the matrix to hydrate and expand, for example by swelling, gelling or effervescing, thereby breaking it open to expose the core and permit the release of the beta 2 adrenergic receptor agonist from the core. In this way, the coating exerts no, or substantially no, influence over the release rate after expiry of the lag time. Preferably coating ingredients include calcium phosphate salts, glyceryl behenate, and polyvinyl pyrollidone, or mixtures thereof, and one or more adjuvants, diluents, lubricants or fillers as described hereinabove.

Preferred components in the coating are as follows, with generally suitable percentage amounts expressed as percentage weight of the coating.

Polyvinyl pyrollidone (Povidone) is preferably present in amounts of about 1 to 25% by weight or the coating, more particularly 4 to 12%, e.g. 6 to 8%.

Glyceryl behenate is an ester of glycerol and behenic acid (a C22 fatty acid). Glyceryl behenate may be present as its mono-, di-, or tri-ester form, or a mixture thereof. Preferably it has an HLB value of less than 5, more preferably approximately 2. It may be present in amounts of about 5 to 85% by weight of the coating, more particularly from 10 to 70% by weight, and in certain preferred embodiments from 30 to 55%.

Calcium phosphate salt may be the dibasic calcium phosphate dihydrate and may be present in an amount of about 10 to 90% by weight of the coating, preferably 20 to 80%, e.g. 40 to 75%.

The coating may contain other common tablet excipients such as fillers, binders and the like, commonly used in forming solid oral dosage forms, such as those described above.

The coating thickness surrounding the core will influence the lag time, and can also affect the rate of drug release thereafter depending on the nature of the coating materials selected.

Press-coating provides a particularly effective means of controlling coating thickness, and therefore controlling the lag time.

Press-coating is particularly advantageous as one can control coat weight, diameter of die and size of core to achieve a precisely defined minimum coating thickness at selected points on the dosage form. Ingress of a physiological medium across the coating at these points will determine the time period for the medium to reach the core and hydrate it, and the lag time may be controlled in this manner.

The thickness of the coating in the plane orthogonal to the direction of compression of the dosage form is carefully selected as it is in this plane that the coating is preferentially infiltrated by the physiological medium and it is in this plane that the tablet will eventually rupture, thereby determining the lag time, after which the contents of the core are released.

The formulator can influence the thickness of the core in this plane and thereby control the lag time. It is important that the coating thickness is identical or substantially so in this plane.

The thickness of the coating in this plane should be about 0.5 to 5 mm, more particularly 1 to 3 mm.

Press-coated dosage forms are generally formed by placing a portion of a powdered coating material in a die and tamping the powder into a compact form using a punch. A preformed core is then deposited onto the compacted coating material before the remainder of the coating material is introduced into the die and compression forces are applied to form the coated dosage form. To ensure that the core is placed on the tamped coating material and to ensure it's correctly positioned in order that the coating thickness will be uniform about the orthogonal plane, it is preferable to employ means for positioning the core in relation to the coating material in a die. Typically such means may be provided by a pin punch or a double punch. A pin punch is a punch that has a convex surface that contacts the coating material to leave a small depression or hollow in the tamped coating material. Thus, when the core is placed into the die on the tamped material, it sits in the depression or hollow and its correct geometry is assured in the final tablet form.

In one embodiment, a cup formed by a pin or double punch is filled with a blend containing the drug substance and then a press coated tablet is subsequently formed.

When selecting coating materials, it is preferred not to employ materials that are swellable or gellable. Typical of such materials are cellulose ethers or cellulosic derivatives such as hydroxyalkyl celluloses, e.g. hydroxypropylmethyl cellulose, or carboxyalkylcelluloses and the like. Such materials tend to form gels which exert a release-controlling effect by forming an erodible barrier through which drug substance may diffuse. Such materials tend to give unreliable lag times and should be avoided in amounts that exert a release-controlling effect. Their release-controlling properties are usually evident when they are employed in amounts of about 10% or greater. Preferably therefore, if any of the aforementioned materials are employed as coating materials they should only be used in small amounts, e.g. less than 10%, more particularly less than 5%, still more particularly less than 1%.

Dosage forms described above may be over-coated with a pharmaceutically acceptable film-coating, for aesthetic purposes (e.g. including a colourant), for stability purposes (e.g., coated with a moisture barrier), for taste-masking purposes, or for the purpose of protecting unstable drug substances from aggressive media, e.g. enteric-coatings.

Press-coated tablets may be prepared by techniques known in the art. A press-coating may be formed by compression using any of the press coaters known in the art. Alternatively, dosage forms may be prepared by granulation and agglomeration techniques, or built up using spray drying techniques, followed by drying.

During compression of the coating around the core, the coating material around the core in the direction of compression is relatively highly compacted and dense. On the other hand, the coating material disposed in the plane orthogonal to the direction of compression is subjected to relatively lower compaction forces and is relatively less dense as a result. Accordingly, the material in this plane is relatively porous and permissive towards the ingress of a physiological medium. Because of the slightly less dense nature of the coating material in this plane, and because the formulator has the latitude to influence the coating thickness, the rate of ingress of the aqueous medium through the coating in this plane can be closely controlled.

Once a physiological medium contacts the core, the core may react by hydrating and swelling and/or gelling or effervescing thereby to break open the coating generally along the direction of ingress of the aqueous media to form to essentially two hemispheres of coating material that may remain conjoined. In this opened form, the dosage form, once ruptured may have the appearance of an opened shell, or the two hemispheres of the coating may become completely detach from each other. The reaction of the core material to the presence of the aqueous medium is likewise in part responsible for controlling the release of the beta 2 adrenergic receptor agonist from the core.

The hardness of the dosage form is preferably at least 40 Newtons, e.g. 40 to 80 Newtons, and more particularly 60 to 75 Newtons. Hardness may be measured according to a process described in The European Pharmacopoeia 4, 2.9.8 at page 201.

Dosage forms having an hardness within this range are mechanically robust to withstand forces generated in the stomach, particularly in the presence of food. Furthermore, the dosage forms are sufficiently porous about the plane orthogonal to the direction of compression to permit ingress of physiological media to the core at an appropriate rate to achieve the lag times referred to herein.

The invention provides in another aspect, a method of forming press-coated dosage forms as herein above described. They may be formed on conventional press coating equipment. Typically such equipment is composed of a series of die are arranged on a rotating platform. The dice are removably mounted in the platform such that differently sized dice may be employed as appropriate. Each die is hollow to receive a lower punch. The punch is positioned, within the die such that the upper surface of the punch and the inner surface of the die define a volume for receiving a precise amount coating material. Once loaded, the platform is rotated until the die is positioned under an upper punch. The upper punch is then urged down onto the coating material under a defined compression force and the coating material is pre-compressed or tamped between the upper and lower punch. A pre-formed core is then fed into die to rest on the tamped coating. Conventional press coating apparatus may be equipped with centering devices that enable cores to be positioned both vertically and radially. This might be achieved by a tamping process, whereby an initial amount of coating material is placed in a die and is tamped with a shaped punch, such as a pin punch, that leaves an indentation in the coating material in which to receive a core. Thereafter, in a second filling operation, a precise amount of coating material is fed into the die to cover the core, and an upper punch compresses the coating material with a defined compaction force to form press-coated dosage forms. The compression force applied during the tamping process is relatively light and is just sufficient to provide a bed of coating material to receive the core and to prevent movement of the coating material as a result of centrifugal force. Subsequent compression to form the dosage form may be adjusted to give a requisite hardness.

Preferably, this compression force is 400 kg, although this may be adjusted by +/−30% in order to give tablets of the required hardness.

The amount of coating material fed into the die can be precisely defined having regard to the density of the coating material, as can the dimension of the die to ensure after compression that the dosage form is formed with the required coating thickness, particularly about the plane orthogonal to the direction of compression. Should it be necessary to change the thickness of the coating, die of appropriate internal dimensions may be placed in the rotating platform, and the amount of coating material fed into the die may be adjusted accordingly.

Suitable rotary tablet machines having high process speeds are known in the art and need no further discussion here.

Cores may likewise be formed using a conventional rotary tablet machine. Cores are preferably compressed under compression forces sufficient to provide cores having a hardness of about 60 Newtons at least, e.g. 50 to 70 Newtons. Cores having hardness in this range give desired release characteristics. If desired, the cores can be formed at the same time as the press coated tablets are produced. In such case, one might employ a Manesty Dry Cota. Such, a press consists of two side-by-side and inter-connected presses where the core is made on one press before being mechanically transferred to the other press for compression coating. Such equipment and techniques for making dosage forms using such equipment are known in the art and no more needs to be said about this here.

Cores are preferably formed according to wet granulation techniques generally known in the art. In a typical procedure, core materials are sieved and blended. Granulating fluid, typically water is then added to the blend and the mixture is homogenized to form a granulate, which is then sprayed dried or dried on a fluid bed drier to obtain a granulate with requisite residual moisture. Preferably the residual moisture content is from about 0.4 to 2.0% by weight. The granulate is then sized by passing it through screens of desired aperture. At this stage, any adjuvants are sized and added to the granulate to form the core composition suitable for compression. The skilled person will appreciate that a coating composition can be formed in an analogous manner.

Press-coated tablets of the invention could also be manufactured as one-step dry coated tablets with a double punch tooling, using for example a Kikusui Seisakusho press, Kyoto Japan.

EXAMPLE 1

A core containing drug substance is prepared for the press coated system as follows. The composition of the core is detailed in Table 1. Lactose monohydrate (Lactose Pulvis [Eta]2O<(R)>, Danone, France and Lactose Fast Flo<(R)> NF 316, Foremost Ing. Group, USA) is a filling agent with interesting technical and functional properties. Lactose Pul- ViS-H2O is used in a blend prepared by wet granulation and Lactose Fast Flo is used in a blend prepared for direct compression. Microcrystalline cellulose (Avicel<R> pH 101, FMC International, Ireland) is used as an insoluble diluent for wet granulation Avicel PH 102 grade is used for direct compression. Polyvinyl pyrrolidone (Kollidon<R> 30, BASF Ludwigshafen, Germany) is a granulating agent, soluble in water, which has the ability of binding the powder particles. Croscarmellose sodium (Ac-Di-Sol<R>, FMC Corporation, USA) is used in the formulation as a super disintegrant. As the external phase, magnesium stearate (Merck, Switzerland) is added as a lubricant and colloidal silicon dioxide (Aerosil" 200, Evonik AG, Germany) in order to improve flow properties of the granular powder.

TABLE 1

Composition of the core

| Ingredients | mg/tablet |
|---|---|
| Terbutaline sulphate (corresponding to 4.1 mg free base) | 5.0 |
| Lactose monohydrate | 20.0 |
| Microcristalline cellulose (Avicel PH101) | 22.0 |
| Povidone (Kollidon30) | 4.0 |
| Sodium Croscarmellose (Ac Di Sol) | 4.0 |
| Magnesiun stearate | 0.6 |
| Colloidal silicon dioxide (Aerosil 200) | 0.3 |
| Ferric oxide | 0.3 |
| Total tablet weight | 56.2 |

The coating material is of a hydrophobic, water insoluble nature. This coating is composed of dibasic calcium phosphate dihydrate (Calipharm, Innophos USA) and glyceryl behenate (Compritol<R> 888ATO, Gattefosse, France). Polyvinylpyrrolidone (Kollidon 30) is a granulating agent, soluble in water, which has the ability of binding the powder particles. Yellow ferric oxide (Sicovit" Yellow 10, BASF, Germany) was added as a dye. A detailed composition of this barrier blend is given in table 2.

TABLE 2

Composition of the coating

| Ingredients | Percent % |
|---|---|
| Dibasic calcium Phosphate dihydrate (Calipharm) | 40.0 |
| Glyceryl behenate (Compritol 888 ATO) | 50.0 |
| Povidone (Kollidon 30) | 8.4 |
| Colloidal silicon dioxide (Aerosil 200) | 0.5 |
| Magnesium stearate | 1.0 |
| Ferric oxide | 0.1 |
| Total | 100.0 |

The required amounts of drug substance A, Ac-Di-Sol<R>, Lactose Pulvis H2O<1>ˆ, Plasdone<R> K29-32 are weighed and manually sieved with a screen having 0.710 mm apertures. The components are homogeneously mixed in a Niro-Fielder PMA 25-liter mixing granulator for 6 min at impeller speed 250 rpm without chopper". Subsequently, the granulating solution (purified water, 25.47% of the weight of the dry blend) is added within 4 min at impeller speed 250 rpm and chopper speed 1500 rpm, using a nozzle H1/4W-95015 (spraying rate of 250 g/min). Mixing is continued for homogenisation and massing of the wet mass for 3 min at impeller speed 500 rpm and chopper speed 3000 rpm. The mixed wet granulate is then dried in a Glatt WSG5 fluidised air drier. The inlet temperature is maintained at 45° C. during drying. The drying duration is 20 min to obtain a granulate with a residual moisture less than 2.5%. The yielded dry granulate is calibrated in a Frewitt MGI 205 granulator using a screen with 0.8 mm apertures for 3 min at speed 244 osc/min (graduation 7). Appropriate amounts of Aerosil<R> 200 and magnesium stearate are manually sieved using a screen with 1.0 mm apertures. Half of the dry granulate is put in a IBC 25 liter followed by Aerosil 200 and then by the other half of the dry granulate. The ingredients are mixed for 10 min at 20 rpm on a Bohle diffusion mixer. Finally, magnesium stearate is added and mixing is continued for 10 min at 20 rpm.

The coating blend is prepared according to the process described below. Batch size for the barrier blend is 13 kg. Weighed amounts of Emcompress<R>, Compritol<R> 888 ATO, Plasdone<R> K29-32 and Sicovit<R> Yellow 10 E 172 are manually sieved with, a screen having 0.710 mm apertures. They are placed in a Niro-Fielder PMA 65-liter mixing granulator. Then, the components are homogeneously mixed for 6 min, at impeller speed 200 rpm, without chopper. Subsequently, the granulating solution (purified water, 8.12% of the weight of the dry blend) is added within 2 min at impeller speed 200 rpm and chopper speed 1500 rpm using a nozzle 4.9 (spraying rate of 520 g/min). Mixing is continued for homogenisation and massing for 1 min at impeller speed 400 rpm and chopper speed 3000 rpm.

The mixed wet granulate is then dried in a Niro-Fielder TSG 2 fluidised air bed dryer. The inlet temperature is maintained at 45 degrees centigrade during drying. The drying lasts 33 min to have residual moisture less than 2.5%. The yielded dry granulate is calibrated in a Frewitt MGI 205 granulator using a screen having 0.8 mm apertures for 4 min at speed 244 osc/min (graduation 7). Appropriate amounts of Aerosil 200 and magnesium stearate are manually sieved using a screen with 1.0 mm apertures. Half of the dry granulate is put in a IBC 25-liter, followed by Aerosil200 and then by the other half of the dry granulate.

The ingredients are mixed for 10 min at 20 rpm on a Bohle diffusion mixer. Finally, magnesium stearate is added and mixing is continued for 10 minutes at 20 rpm.

440 mg of coating blend is press coated on a core to provide press coated tablets (9 mm diameter). 305 mg of coating blend is press coated on a core to provide press coated tablets (8 mm diameter). These different press coatings are made utilising a Kilian RUD tableting machine. First and second loading hoppers are filled up with the coating granulate. Between the two loading hoppers, the machine is equipped with a transfer system adapted to feed the cores. For each tablet, the first loading hopper supplies with about half of the quantity to be applied to the core. Then, the feeding system provides and positions a core centered in the die. Subsequently, the second loading hopper supplies with the other half of the quantity to be applied to the core. The compression step then occurs.

EXAMPLE 2

The in vitro dissolution profile of a tablet containing a 5 mg loading of drug substance A prepared according to the method of Example 1 is determined using USP dissolution apparatus No. II (paddles) using stationary baskets and applying a stirring rate of 100 rpm. The dissolution medium is simulated intestinal fluid (SIF), with a volume of 900 ml.

FIG. 1 shows the release profiles of several tablets formed according to the above formulation and methodology. The

EXAMPLE 3

Step 1 Cores corresponding to Table 1 were loaded into a conventional perforated pan coater and sprayed with a with a 7% w/w aqueous solution of hydroxypropyl methylcellulose type 2910 (Pharmacoat 603) and polyethylene glycol 400, in a weight ratio of 10:1. Coating continued until a weight gain of 3% of total tablet weight is achieved Step 2 the cores were then coated by a powder layering technique spreading a powder mixture containing hydroxypropyl methylcellulose type 2910, (Methocel E50), talc and silicon dioxide using similar solution of step 1 as binder solution. Coating continued until a weigh gain of 45% of total tablet weight is achieved.

EXAMPLE 4

The in vitro dissolution profile of a tablet containing a 2.5 mg loading of drug substance A prepared according to the method of Example 3 is determined using USP dissolution apparatus No. 2 (paddles) and stationary baskets and applying a stirring rate of 100 rpm. The dissolution medium is simulated intestinal fluid (SIF), with a volume of 900 ml.

Figure 2:
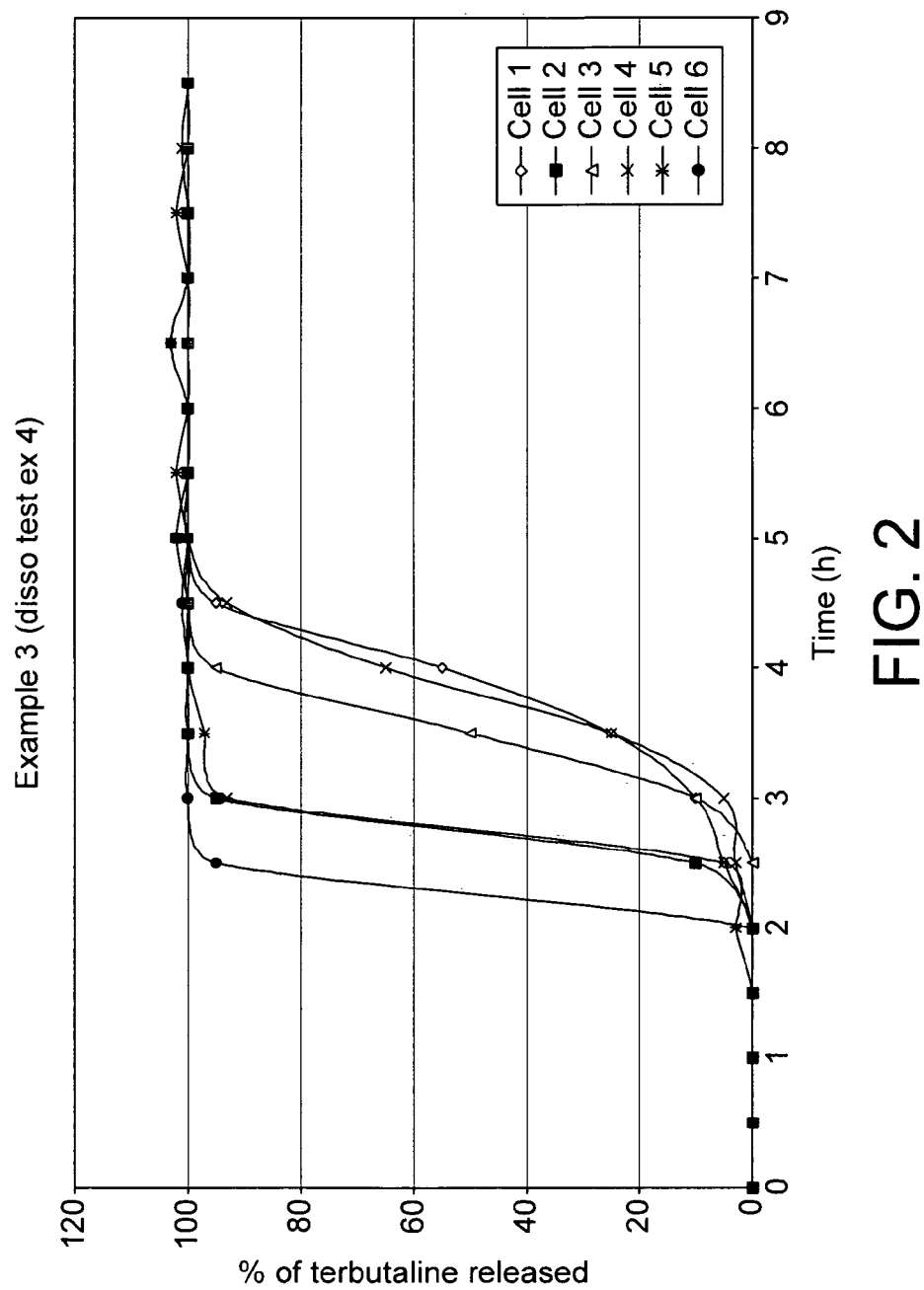

FIG. 2 shows the release profiles of several tablets formed according to the above formulation and methodology. The figure clearly shows that it is possible to obtain lag times with a very high degree of precision.

EXAMPLE 5

Cores corresponding to Table 1 are loaded into a conventional perforated pan coater and sprayed with a with a 5% w/w hydroalcoholic solution of ethylcellulose and triethyl citrate (TEC), in a weight ratio of 5:1. Coating continued until a weight gain of 20% of total tablet weight is achieved

EXAMPLE 6

The in vitro dissolution profile of a tablet containing a 2.5 mg loading of drug substance A prepared according to the method of Example 5 is determined using USP dissolution apparatus No. 2 (paddles) and stationary baskets and applying a stirring rate of 100 rpm. The dissolution medium is simulated intestinal fluid (SIF), with a volume of 900 ml.

FIG. 3 shows the release profiles of several tablets formed according to the above formulation and methodology. The figure clearly shows that it is possible to obtain lag times with a very high degree of precision.

EXAMPLE 7 a) Lactose Non pareil beads are loaded in a bottom spray fluid bed drier (Glatt AG Pratteln Switzerland) and sprayed first with a 5% aqueous solution of terbutaline sulphate and then with a 5% w/w hydroalcoholic solution of ethylcellulose and triethyl citrate (TEC), in a weight ratio of 10:1. Coating continued until a weight gain of 30% is achieved b) Lactose non pareil beads are loaded in a bottom spray fluid bed drier (Glatt AG Pratteln Switzerland) and sprayed first with a 5% aqueous solution of terbutaline sulphate and then with a 5% w/w hydroalcoholic solution of ethylcellulose and triethyl citrate (TEC), in a weight ratio of 5:1. Coating continued until a weight gain of 30% is achieved c) Hard shell capsules (Capsugel Colmar France) are then filled with MG Futura (Bologna Italy) capsule filling machine with amount of coated beads (50% step a—50% step b) corresponding to 5 mg of terbutaline sulphate.

EXAMPLE 7

The in vitro dissolution profile of a capsule containing a 5 mg loading of drug substance A prepared according to the method of Example 7 is determined using USP dissolution apparatus No. II (paddles) using stationary baskets and applying a stirring rate of 100 rpm. The dissolution medium is simulated intestinal fluid (SIF), with a volume of 900 ml.

FIG. 4 shows the release profiles of several capsules formed according to the above formulation and methodology. The figure clearly shows that it is possible to obtain lag times with a very high degree of precision.

The invention claimed is:

1. A method of treating nocturnal hypoglycaemia in a human subject, the method comprising administering a modified release oral dosage form containing a beta 2 adrenergic receptor agonist to the subject, the modified release oral dosage from being adapted to release the beta 2 adrenergic receptor agonist after a lag time of 1 to 3 hours after administration to the subject and during which lag time substantially none of the beta 2 adrenergic receptor agonist is released.

2. The method of claim 1, wherein said dosage from, provides a time (Tmax) to mean peak plasma concentration (Cmax) between 1 hour and 6 hours after administration of said dosage form.

3. The method of claim 1, wherein the dosage form, when tested in an in-vitro simulated intestinal fluid, releases the beta 2 adrenergic receptor agonist over a period of time defined by an in vitro dissolution profile wherein not more than 10% of the dose is released after 1 or 2 hours, at least 80% is released after 6 hours, and at least 100% is released after 10 hours.

4. The method of claim 3, wherein the in vitro simulated intestinal fluid is a phosphate buffer at pH 6.8 and the dissolution profile is obtained using the USP apparatus II with paddle rotation at 100 rpm.

5. The method of claim 1, wherein no more than about 10% of the beta 2 adrenergic receptor agonist is released during the lag time.

6. The method of claim 1 wherein the beta 2 adrenergic receptor agonist is administered in a dosage of 0.1 to 10 mg once a day before bedtime and simultaneously with food or after food.

7. The method of claim 1 wherein the beta 2 adrenergic receptor agonist is terbutaline sulphate.

8. The method of claim 7 wherein the dosage formachieves for a dose of 5 mg terbutaline sulphate a mean peak plasma concentration (Cmax) of terbutaline of about 3 to 9 ng/ml, and a mean $AUC_{0-48}$ of about 14 to 68 hr.ng/ml.

* * * * *

UNITED STATES PATENT AND TRADEMARK OFFICE
CERTIFICATE OF CORRECTION

PATENT NO. : 8,697,755 B2
APPLICATION NO. : 13/384388
DATED : April 15, 2014
INVENTOR(S) : Guy Vergnault It is certified that error appears in the above-identified patent and that said Letters Patent is hereby corrected as shown below:

In the Claims

At column 20, line number 32, claim 2, please correct the word "from" to read "form".

Signed and Sealed this
Twenty-fourth Day of June, 2014

Michelle K. Lee
*Deputy Director of the United States Patent and Trademark Office*